(12) United States Patent
Sebag et al.

(10) Patent No.: US 12,656,327 B2
(45) Date of Patent: Jun. 16, 2026

(54) METHOD FOR THE QUANTIFICATION AND CHARACTERIZATION OF CARBON IN SOILS

(71) Applicant: IFP Energies nouvelles, Rueil-Malmaison (FR)

(72) Inventors: David Sebag, Rueil-Malmaison Cedex (FR); Isabelle Kowalewski, Rueil-Malmaison Cedex (FR); Violaine Lamoureux-Var, Rueil-Malmaison Cedex (FR); Daniel Pillot, Rueil-Malmaison Cedex (FR); Herman Ravelojaona, Rueil-Malmaison Cedex (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 477 days.

(21) Appl. No.: 18/551,229

(22) PCT Filed: Mar. 14, 2022

(86) PCT No.: PCT/EP2022/056458
§ 371 (c)(1),
(2) Date: Sep. 19, 2023

(87) PCT Pub. No.: WO2022/200093
PCT Pub. Date: Sep. 29, 2022

(65) Prior Publication Data
US 2024/0110906 A1 Apr. 4, 2024

(30) Foreign Application Priority Data

Mar. 26, 2021 (FR) ...................................... 2103114

(51) Int. Cl.
*G01N 31/12* (2006.01)
*G01N 33/24* (2006.01)

(52) U.S. Cl.
CPC ........... *G01N 33/241* (2013.01); *G01N 31/12* (2013.01)

(58) Field of Classification Search
CPC ....... G01N 33/241; G01N 31/12; G01N 33/24
See application file for complete search history.

(56) References Cited

U.S. PATENT DOCUMENTS

| | | | |
|---|---|---|---|
| 3,953,171 A | 4/1976 | Espitalie et al. | |
| 2015/0247787 A1* | 9/2015 | Yeomans | G01N 5/045 73/865 |

(Continued)

FOREIGN PATENT DOCUMENTS

| | | |
|---|---|---|
| FR | 2227797 A5 | 11/1974 |
| FR | 2472754 A1 | 7/1981 |

OTHER PUBLICATIONS

English Written Opinion—PCT/EP2022/056458. (Year: 2022).*

(Continued)

*Primary Examiner* — Brian J. Sines
(74) *Attorney, Agent, or Firm* — Fitch, Even, Tabin & Flannery LLP

(57) ABSTRACT

The invention relates to a method of characterizing and of quantifying carbon from a superficial deposit, wherein a sample of the deposit is subjected to heating in an inert atmosphere, the sample residue is subjected to heating in an oxidizing atmosphere, and quantities of HC, CO and $CO_2$ released during heating, from which standard parameters TOC and MinC, and a ratio between mineral carbon and total carbon of the sample are determined, are measured. If the ratio is non-zero, the organic carbon content is equal to the sum of TOC and of a percentage of TOC ranging between 4 and 12%, and the mineral carbon content is equal to MinC minus this percentage of TOC. If the ratio is zero, (Continued)

the mineral carbon content is zero and the organic carbon content is equal to the sum of TOC and MinC.

18 Claims, 5 Drawing Sheets

(56) References Cited

U.S. PATENT DOCUMENTS

| | | | | |
|---|---|---|---|---|
| 2016/0047783 A1* | 2/2016 | Sato | .......................... | G01N 31/12 |
| | | | | 422/51 |
| 2022/0412945 A1* | 12/2022 | Romero-Sarmiento | ....................... | |
| | | | | G01N 33/241 |
| 2024/0183837 A1* | 6/2024 | Sebag | ...................... | G01N 1/44 |

OTHER PUBLICATIONS

Behar F., Beaumont V., De B., Penteado H.L. (2001) Rock-Eval 6 Technology: Performances and Developments, Oil & Gas Science and Technology 56, 111-134.

Disnar, J.R., Guillet, B., Keravis, D., Di-Giovanni, C., Sebag, D., 2003. Soil organic matter (SOM) characterization by Rock-Eval pyrolysis: scope and limitations. Organic Geochemistry 34, 327-343.

Malou, O.P., Sebag, D., Moulin P., Chevallier, T., Badiane-Ndour, N.Y., Thiam, A., Chapuis-Lardy, L. 2020. The Rock-Eval® signature of soil organic carbon in Arenosols of the Senegalese groundnut Basin. How do agricultural practices matter? » Agriculture, Ecosystems & Environment 301: 107030. https://doi.org/10.1016/j.agee.2020.107030.

Pilot, D., Deville, E., Prinzhofer, A., 2014. Identification and Quantification of Carbonate Species Using Rock-Eval Pyrolysis. Oil & Gas Science and Technology—Revue d'IFP Energies nouvelles 69, 341-349.

Sebag, D., Disnar, J.R., Guillet, B., Di Giovanni, C., Verrecchia, E.P., Durand, A., 2006. Monitoring organic matter dynamics in soil profiles by "Rock-Eval pyrolysis": bulk characterization and quantification of degradation. European Journal of Soil Science 57, 344-355.

Sebag, D., Verrecchia, E.P., Cécillon, L., Adatte, T., Albrecht, R., Aubert, M., Bureau, F., Cailleau, G., Copard, Y., Decaëns, T., Disnar, J-R., Hetényi, M., Nyilas, T., Trombino, L., 2016. Dynamics of soil organic matter based on new Rock-Eval indices. Geoderma 284, 185-203.

International Search Report for PCT/EP2022/056458, dated May 9, 2022; 3 pages.

Written Opinion for PCT/EP2022/056458, dated May 9, 2022; 6 pages.

Johannes, I. et al., Evaluation of oil potential and pyrolysis kinetics of renewable fuel and shale samples by Rock-Eval analyzer, ScienceDirect, Jan. 10, 2007; 8 pages.

* cited by examiner

[Fig. 1A]
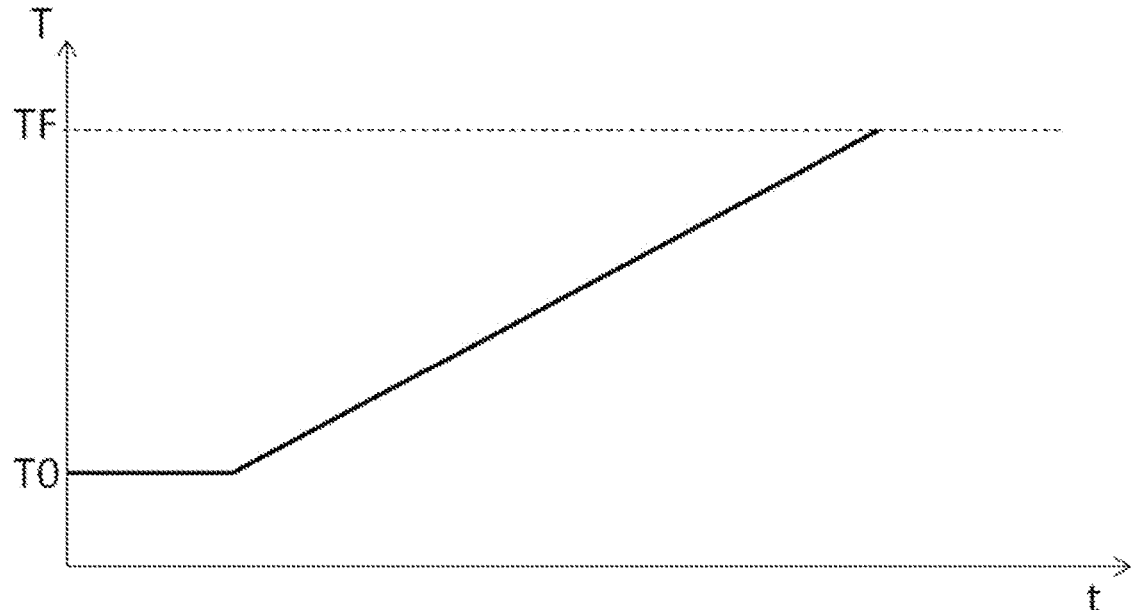
[Fig. 1B]
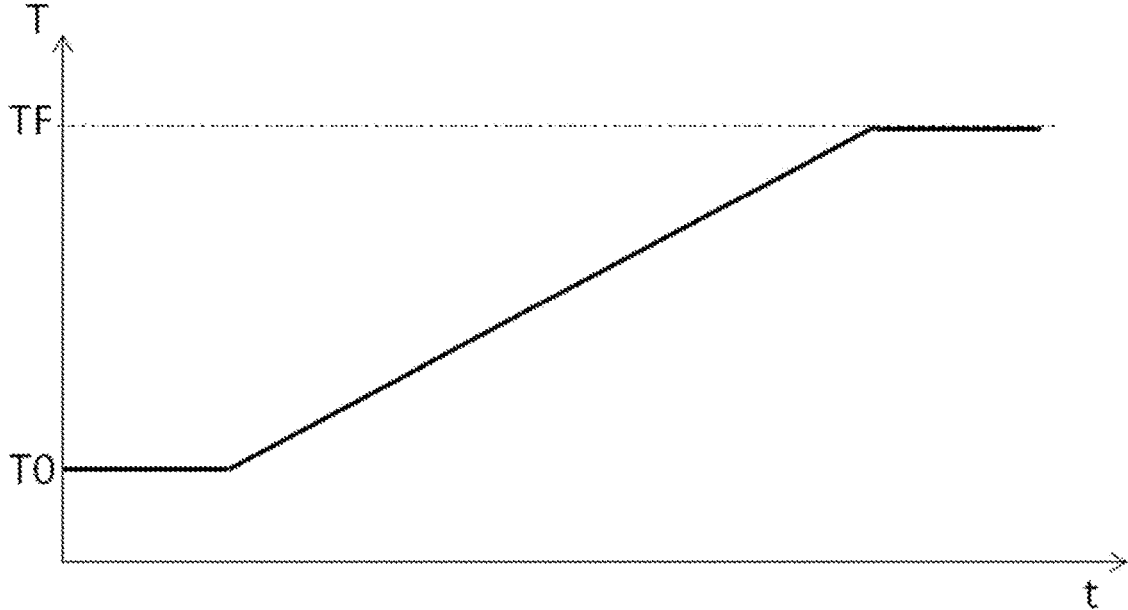

[Fig. 2A]
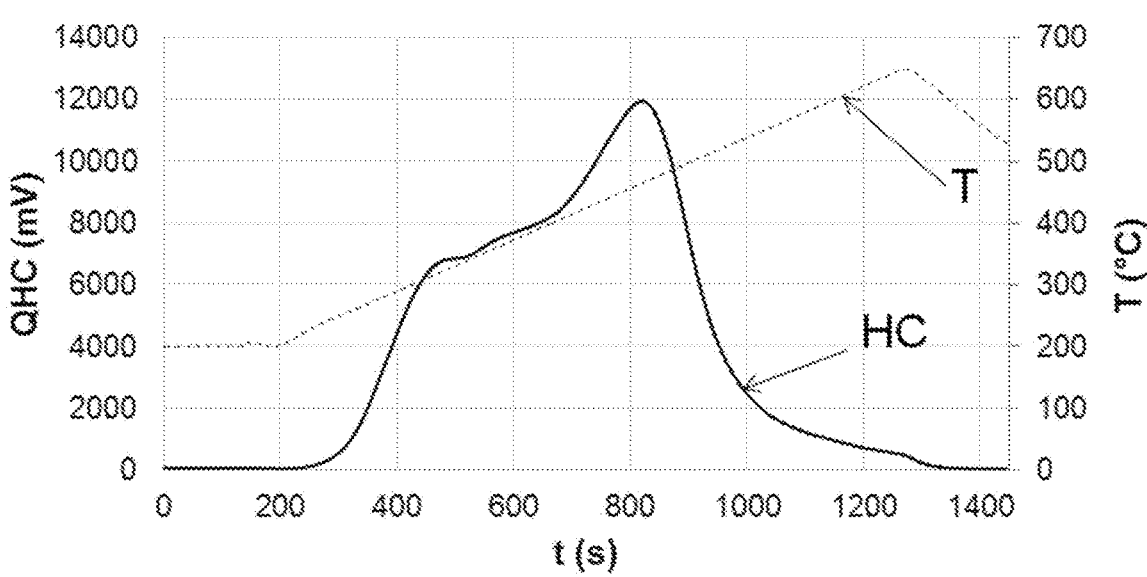
[Fig. 2B]
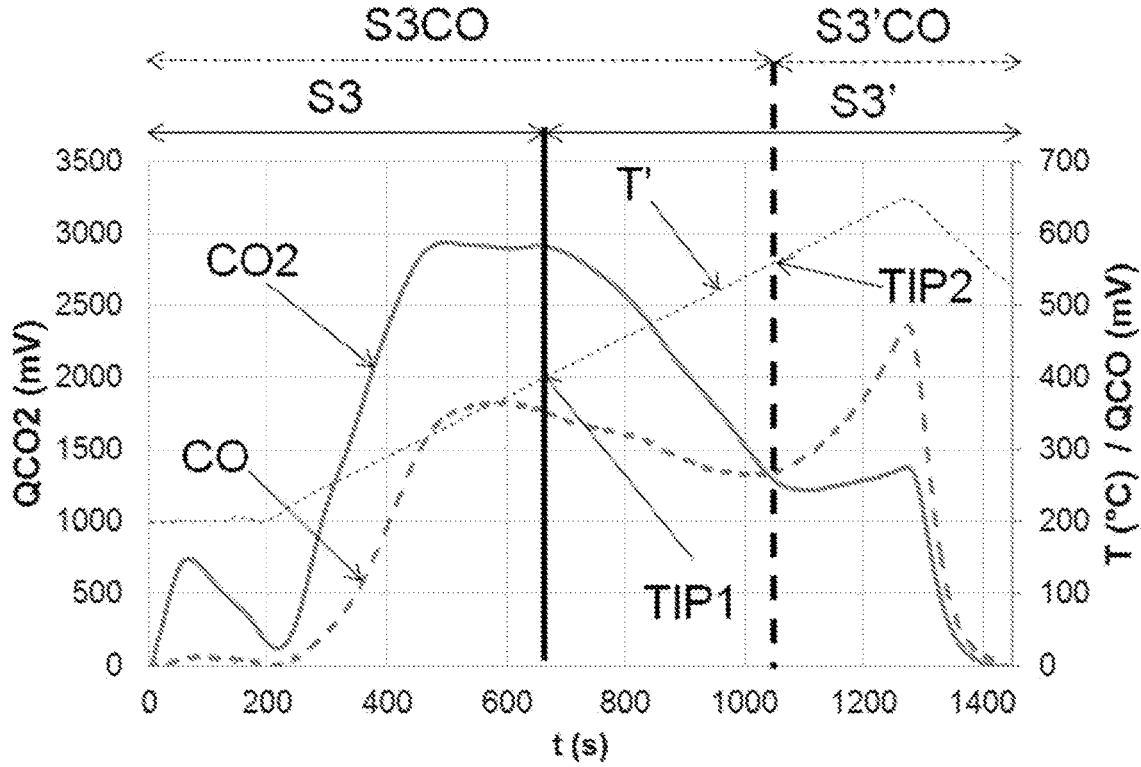

[Fig. 2C]
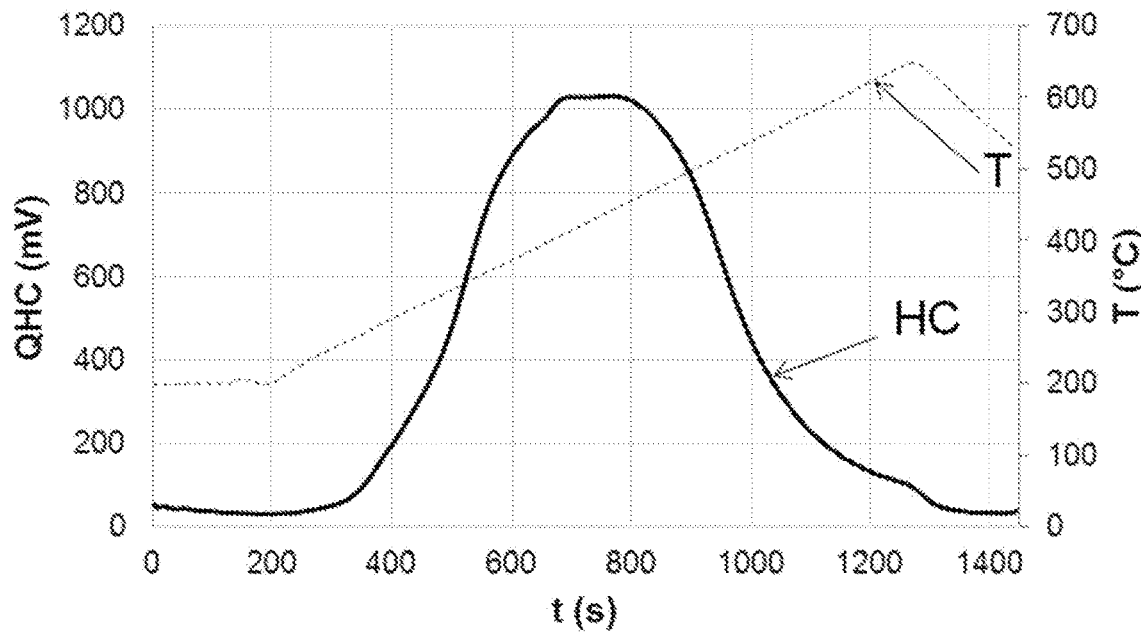
[Fig. 2D]
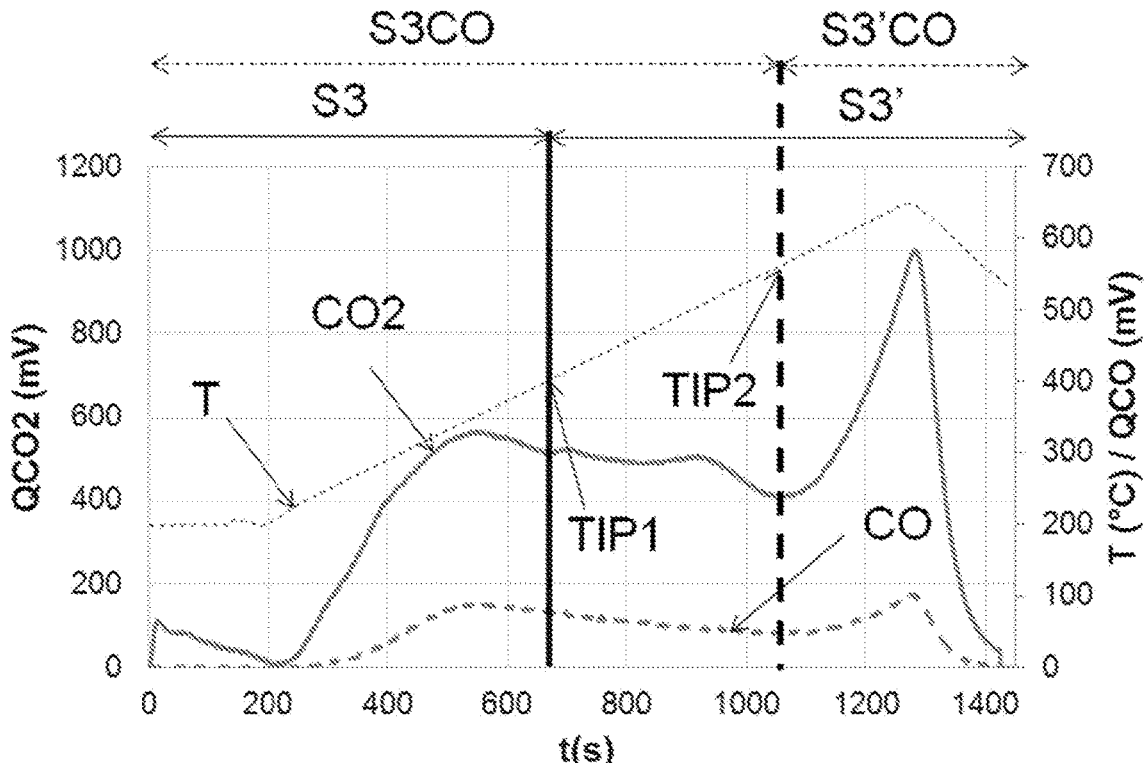

[Fig. 3A]
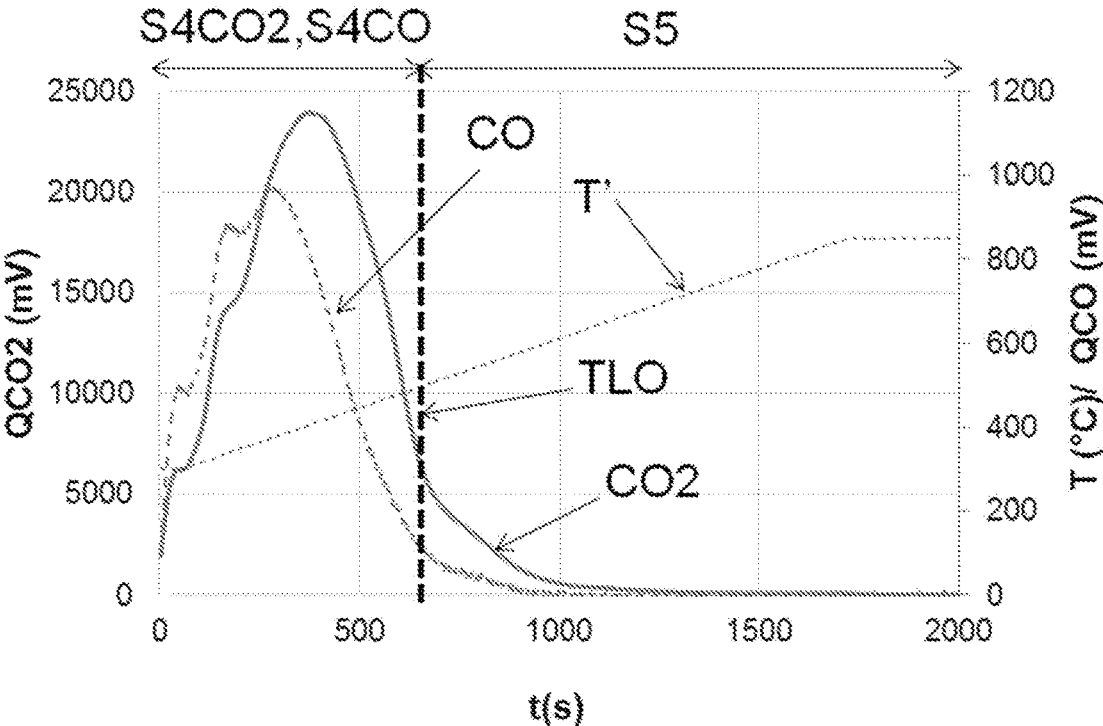
[Fig. 3B]
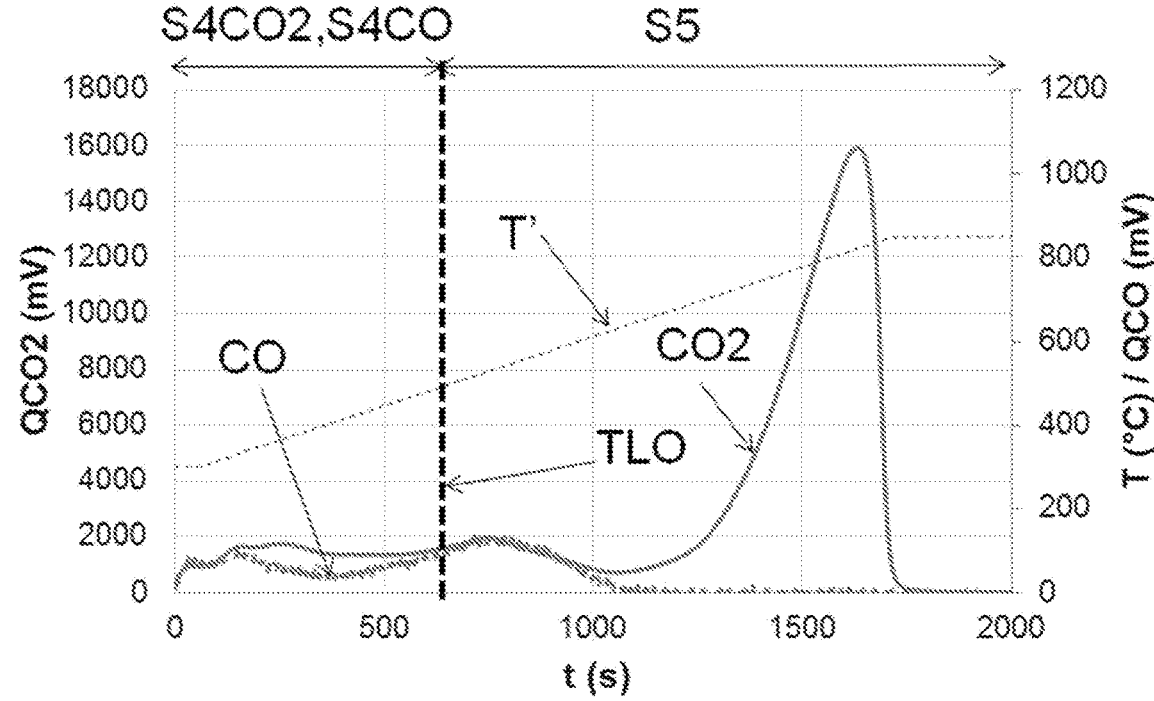

[Fig. 4]
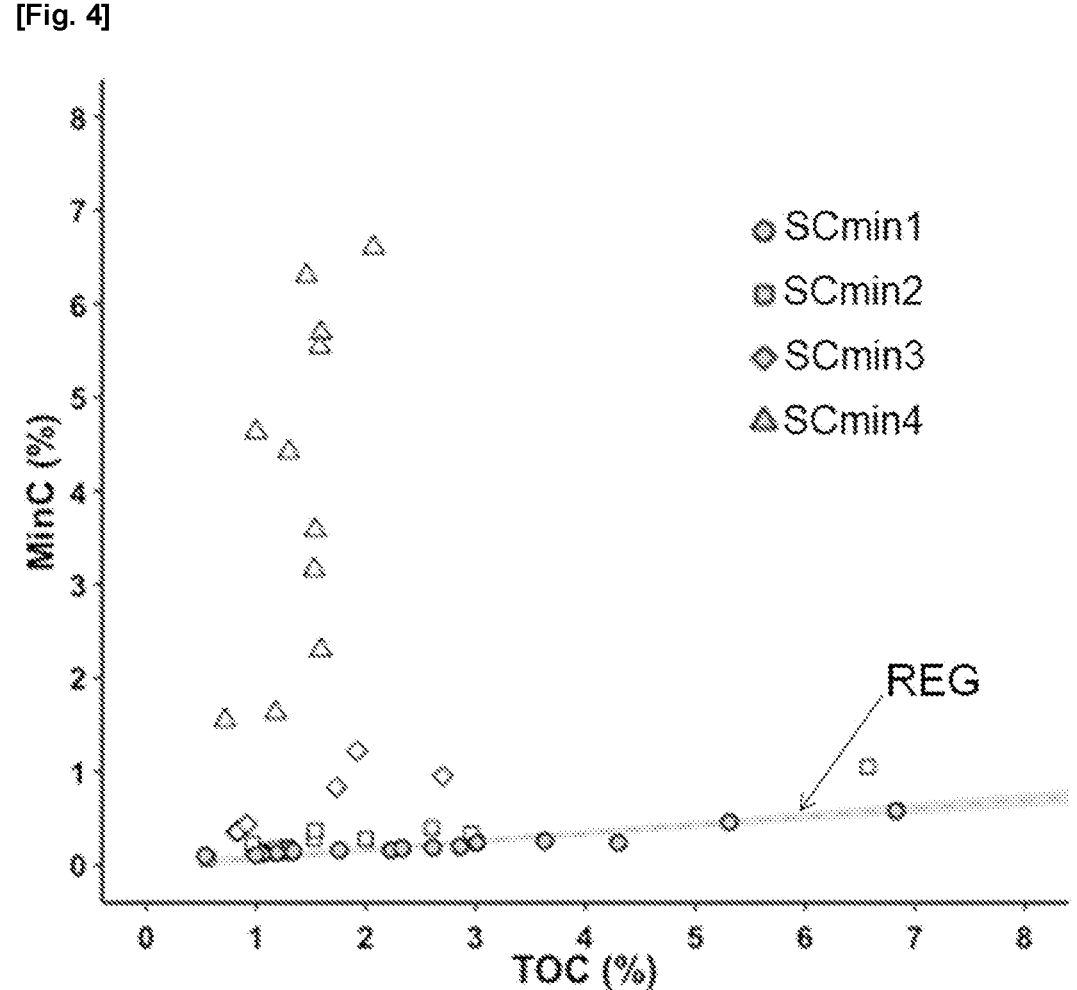

1

METHOD FOR THE QUANTIFICATION AND CHARACTERIZATION OF CARBON IN SOILS

CROSS-REFERENCE TO RELATED APPLICATIONS

Reference is made to PCT/EP2022/056458 filed Mar. 14, 2022, and French Patent Application No. 2103114 filed Mar. 26, 2021, which are incorporated herein by reference in their entirety.

BACKGROUND OF THE INVENTION

Field of the Invention

The present invention relates to the field of soil science and environmental geosciences. More specifically, it concerns the characterization of carbon contained in superficial deposits, and notably in soils.

Description of the Prior Art

In order to meet ecological challenges or to comply with some environmental laws and directives, professionals in the field of soil science and environmental geosciences (research laboratories, design offices, environmental agencies, farm operators) are increasingly led to establish protocols for monitoring the impact of human activities on carbon stocks in soils and in eco-agrosystems. These impact studies and monitoring require the ability to study large sample series in relatively short times in relation to conventionally employed methodologies. In addition, these methods are often accompanied by environmental and security constraints that increase the deadlines and the analytical costs, and which often require hiring specialized service providers (analysis laboratories for example).

The organic forms of carbon stored in superficial deposits, notably in soils, represent a major challenge for agriculture and climate. Indeed, they play a key role on the structural quality and the fertilizing value of soils and they are notably involved in the carbon cycle by representing the largest reservoir of the Earth's organic carbon. Ensuring the food security of populations and promoting organic carbon sequestration in soils requires finding a compromise between maintaining organic matter stocks labile enough to release the nutrients needed for plant growth and promoting the storage of carbon forms resistant enough to mitigate in the long term the anthropogenic emissions of greenhouse gases.

Inorganic forms of carbon are of variable mineralogy. Essentially represented by calcium (Ca) carbonates and oxalates in soils, they may sometimes involve other cations (Fe in siderite, Mg in dolomite, etc.), notably in a tropical environment. Irrespective of their role in biogeochemical cycles (notably as carbon sinks), the mineral forms of carbon pose technical problems for the analysis of organic forms. Indeed, no routine method makes it possible to characterize the various carbon forms with a single measurement, and the conventionally employed approaches are based on specific extractions and separations (acid fumigation, Walkley-Black method, Bernard calcimeter method), followed by targeted analyses using specialized scientific equipment (CHN elemental analysis, IR spectrometry, GC-MS, $^{13}$C-NMR).

Methods for thermal analysis of the organic matter of soils based on measurements of quantities of hydrocarbon compounds (HC) and at least one of carbon monoxide (CO) and of carbon dioxide ($CO_2$) released over time by a sample subjected to a heating sequence in an inert atmosphere, then or to a heating sequence in an oxidizing atmosphere, are also known. These methods were initially developed in the oil industry for the purposes of characterization of the organic fraction of sedimentary rocks. The ROCK-EVAL® device (IFP Energies nouvelles, France) developed by the applicant and notably described in patents FR-2,227,797 (U.S. Pat. No. 3,953,171) and FR-2,472,754 (U.S. Pat. No. 4,352,673) is thus known, which comprises a pyrolysis oven distinct from an oxidation oven, a flame ionization type detector (FID) for detecting hydrocarbon compounds (HC) and an infrared type detector (IR) for detecting at least one of carbon monoxide (CO) and carbon dioxide ($CO_2$). Methods developed for particular applications in the oil industry, having each their own heating temperature sequence for at least one of pyrolysis and heating in an oxidizing atmosphere, are also known. The ROCK-EVAL® BULK ROCK method, more particularly dedicated to conventional mother rock samples (Behar et al., 2001), is notably known. The inert-atmosphere heating sequence of this method is characterized by an initial temperature T1 of the pyrolysis oven generally ranging between 300° C. and 350° C., a temperature that is maintained for a predetermined period of time of a few minutes. It is during this phase that the so-called "free" hydrocarbons (actually corresponding to hydrocarbons of low to high molecular weight) initially contained in the rock sample are released. Their quantity is assessed by measuring the area of a first peak, denoted by $S_1$, of the curve (also referred to as thermogram) representing the quantity of hydrocarbon compounds released during the heating sequence in an inert atmosphere. The pyrolysis temperature is subsequently increased progressively up to a temperature T2 of generally 650° C. During this phase, volatilization of the very heavy hydrocarbon compounds and cracking of the non-volatile organic matter (kerogen) take place. The quantity of hydrocarbon compounds released during this thermal cracking phase is assessed by measuring the area of a second peak, denoted by $S_2$. In parallel, the quantities of CO and $CO_2$ are measured and also represented in the form of curves. These curves have two peaks conventionally denoted by S3CO (respectively S3$CO_2$), considered to correspond to the CO (respectively the $CO_2$) generated by cracking the organic matter of the sample during heating in an inert atmosphere, and S3'CO (respectively S3'$CO_2$), considered to correspond to the CO (respectively the $CO_2$) generated by the thermal decomposition of the carbonate forms (notably calcite) during heating in an inert atmosphere. The sample residue resulting from heating in an inert atmosphere is then subjected to heating in an oxidizing atmosphere from a temperature ranging between about 300° C. and 400° C., preferably equal to 300° C. The temperature of the sample residue considered is raised according to a temperature gradient ranging between 20° C. and 40° C./min, up to an oxidation end temperature ranging between 750° C. and 950° C., which is preferably equal to 850° C. During this heating sequence in an oxidizing atmosphere, the quantities of CO and of $CO_2$ released by the sample residue are measured and represented as curves, leading to a peak conventionally denoted by S4CO (respectively S4$CO_2$), which is considered to correspond to the quantity of CO (respectively $CO_2$) generated by the combustion of the organic matter during the oxidation cycle. From these measurements, this method defines standard parameters, in particular the parameter denoted by TOC (Total Organic Carbon), which corresponds to the carbon content of the sample, determined from the total quantity of HC released by the sample and the quantities of CO and $CO_2$ released below threshold temperatures during the pyrolysis phase and the oxidation phase; and the parameter denoted by MinC (Mineral Carbon), which corresponds to the mineral carbon content of the sample, determined from the quantities of CO and $CO_2$ released by the sample above threshold temperatures during the pyrolysis phase and the oxidation phase.

The following documents are mentioned in the description:

Behar F., Beaumont V., De B., Penteado H. L. (2001) Rock-Eval 6 Technology: Performances and Developments, Oil & Gas Science and Technology 56, 111-134.

Disnar, J. R., Guillet, B., Keravis, D., Di-Giovanni, C., Sebag, D., 2003. Soil Organic Matter (SOM) Characterization by Rock-Eval Pyrolysis: Scope and Limitations. Organic Geochemistry 34, 327-343.

Malou, O. P., Sebag, D., Moulin P., Chevallier, T., Badiane-Ndour, N. Y., Thiam, A., Chapuis-Lardy, L. 2020. The Rock-Eval® signature of soil organic carbon in Arenosols of the Senegalese groundnut Basin. How do agricultural practices matter?»*Agriculture, Ecosystems & Environment* 301: 107030. https://doi.org/10.1016/j.agee.2020.107030.

Pillot, D., Deville, E., Prinzhofer, A., 2014. Identification and Quantification of Carbonate Species Using Rock-Eval Pyrolysis. Oil & Gas Science and Technology—Revue d'IFP Energies nouvelles 69, 341-349.

Sebag, D., Disnar, J. R., Guillet, B., Di Giovanni, C., Verrecchia, E. P., Durand, A., 2006. Monitoring Organic Matter Dynamics in Soil Profiles by "Rock-Eval pyrolysis": Bulk Characterization and Quantification of Degradation. European Journal of Soil Science 57, 344-355.

Sebag, D., Verrecchia, E. P., Cécillon, L., Adatte, T., Albrecht, R., Aubert, M., Bureau, F., Cailleau, G., Copard, Y., Decaëns, T., Disnar, J.-R., Hetényi, M., Nyilas, T., Trombino, L., 2016. Dynamics of Soil Organic Matter based on new Rock-Eval indices. Geoderma 284, 185-203.

Since the 2000s, this type of analyses has also been used and adapted to study the organic fraction of superficial deposits and notably of soils.

For example, prior art contains the method described in the document (Disnar et al., 2003), which provides an adaptation of the pyrolysis heating sequence consisting of an initial temperature of the inert-atmosphere heating sequence of 200° C., instead of 300° C. in the ROCK-EVAL® BULK ROCK method described above. This lower initial temperature allows extension of peak S2 defined above to the cracking temperatures of the most thermolabile organic components. Indeed, these thermolabile constituents are much more abundant in superficial deposits than in sedimentary rocks. To assess their contribution and thus to evaluate the thermal stability of the organic matter, this method defines the parameter R400 that measures the relative proportion of peak S2 corresponding to the temperatures below 400° C. Besides, this document also highlights a negative difference between parameter TOC as defined in the ROCK-EVAL® BULK ROCK method and the organic carbon contents measured with standardized methods (elemental analyses for example), and it recommends a statistical correction (that is application of a correction coefficient established on a representative panel of soil samples) to correct parameter TOC, defined for the oil industry, so that it is really representative of the organic carbon content, notably for samples rich in poorly decomposed organic matter in relation to their biogenic precursors (litters, composts, peats, etc.).

Also known is the document (Sebag et al., 2006), which uses this adapted heating sequence and provides in addition a deconvolution of peak S2 to assess the degree of decomposition of the organic constituents. Indeed, the thermograms of the superficial deposits, in particular of organic samples, show a plurimodal distribution whose major modes always are in particular temperature ranges (300-320° C.; 360-380° C.; 420-440° C.; 470-490° C. and 540-560° C.). The method described in this document decomposes peak S2 into five elementary Gaussian distributions centered on these modes. This mathematical deconvolution amounts to assessing the relative contribution to peak S2 of each elementary distribution considered as relative to a class of constituents defined by their only cracking temperature. These elementary contributions are subsequently used to calculate new parameters that measure the overall thermal stability of the organic matter (R-index) and the degree of decomposition of the thermolabile fraction (I-index). However, the deconvolution method is based on an iterative approach for adjusting the position and the area of each elementary distribution according to arbitrarily set statistical parameters, which reduces the reproducibility of the decomposition.

Prior art also includes the document (Sebag et al., 2016), which describes an alternative approach showing that an integration of the thermograms representative of the quantity of HC contained in the sample by temperature bands (200-340° C.; 340-400° C.; 400-460° C.; 460-520° C. and 520-650° C.) leads to results comparable to the mathematical deconvolution, which are, moreover, perfectly reproducible. This approach has been used for many applications, but it suffers from some intrinsic limits. First, it is based on the definition of empirically defined threshold temperatures so that the area of each temperature band best approximates the area of the corresponding elementary distribution obtained by deconvolution. Moreover, these areas and the parameters resulting therefrom only provide qualitative information insofar as they all correspond to relative proportions or to relative proportion ratios. Finally, this approach is limited to the consideration of the quantities of HC released during the pyrolysis phase, whereas the majority of the carbon is represented by the CO and the $CO_2$ released during pyrolysis and oxidation phases.

Furthermore, despite these adaptation or improvement attempts, the known methods do not provide standard parameter values TOC and MINC respectively representative of the organic carbon and mineral carbon content of a sample in the case of superficial deposits. Indeed, parameter TOC (respectively MINC) of the ROCK-EVAL® BULK ROCK method measures the carbon content from the quantities of CO and $CO_2$ released below (respectively above) threshold temperatures considered as thermal limits between the organic and mineral forms of carbon.

Now, this definition is inaccurate, whether for carbonate or non-carbonate formations. Indeed, as shown in the document (Malou et al., 2020), this definition notably involves the systematic calculation of a parameter MINC, even for samples with no mineral carbon form. However, more generally, as observed by the applicant, this implies that, even in samples containing mineral carbon forms, a part of parameter MINC results from the thermal cracking of organic constituents above threshold temperatures. Finally, as shown in the document (Pillot et al., 2014), some mineral forms of carbon (such as siderite or oxalates) are likely to decompose at temperatures below the threshold temperatures used for calculating standard parameters TOC and MINC.

SUMMARY OF THE INVENTION

The present invention aims to overcome the drawbacks related to the use of a method initially developed for the oil industry for analysis of the organic matter in superficial deposits, and notably in soils. In particular, the present invention defines a modified inert-atmosphere heating sequence, in form of a thermal gradient, which therefore is suited to implement and better suited to superficial deposit samples. An optional oxidizing-atmosphere heating sequence, also better suited to superficial deposit samples, is further described in the present invention. Moreover, the present invention defines corrections to be applied to parameters TOC and MinC determined according to the prior art, so as to determine organic carbon and mineral carbon contents that are closer to the organic carbon and mineral carbon contents determined by standardized methods.

The present invention thus enables fast, simple and reliable characterization of the carbon forms present in a sample of a superficial deposit, using corrected standard parameters.

The present invention relates to a method of characterizing and quantifying the carbon present in a superficial deposit, from a sample representative of the superficial deposit, wherein at least the following steps are applied to the sample:

A. heating the sample according to a first heating sequence in an inert atmosphere, and continuously measuring a quantity of hydrocarbon compounds, a quantity of CO and a quantity of $CO_2$ released during the first heating sequence, the first heating sequence in an inert atmosphere comprising at least one isothermal stage of predetermined duration at an initial temperature (T0) followed by a thermal gradient in order to reach a final temperature (TF), the initial pyrolysis temperature (T0) ranging between 80° C. and 200° C., the final pyrolysis temperature (TF) ranging between 600° C. and 650° C.;

B. heating a residue of the sample from the first heating sequence according to a second heating sequence in an oxidizing atmosphere, and measuring a quantity of CO and a quantity of $CO_2$ released during the second heating sequence, the second heating sequence in an oxidizing atmosphere starting at an initial temperature ranging between 150° C. and 300° C., and ending at a final temperature ranging between 850° C. and 1200° C., following a thermal gradient;

C. determining a value of a parameter SCmin representative of a mineral carbon proportion in relation to the total carbon of the sample, from a ratio between the quantity of $CO_2$ released by the residue of the sample above an intermediate temperature of the second heating sequence ranging between 620° C. and 680° C., and the quantity of $CO_2$ released by the residue during the second heating sequence;

D. from the measurements of the quantities of HC, CO and $CO_2$ released during the first and second heating sequences, determining parameters defined with formulas of the type:

$$TOC = [S2*0.083] + \left[S3*\frac{12}{440}\right] + \left[\left(S3CO + \frac{S3'CO}{2}\right)*\frac{12}{180}\right] +$$

$$\left[S4CO_2*\frac{12}{440}\right] + \left[S4CO*\frac{12}{280}\right]$$

-continued $$Min\,C = \left[S3'*\frac{12}{440}\right] + \left[\frac{S3'CO}{2}*\frac{12}{280}\right] + \left[S5*\frac{12}{440}\right]$$

where S2 represents the quantity of HC released during the first heating sequence, S3 and S3' represent the quantities of $CO_2$ released during the first heating sequence respectively up to and above a first intermediate temperature of the first heating sequence ranging between 370° C. and 430° C., S3CO and S3'CO represent the quantities of CO released during the first heating sequence respectively up to and above a second intermediate temperature of the first heating sequence ranging between 520° C. and 580° C., S4$CO_2$ and S4CO represent the quantities respectively of $CO_2$ and CO released during the second heating sequence up to the intermediate temperature of the second heating sequence, and S5 represents the quantity of $CO_2$ released during the second heating sequence above the intermediate temperature of the second heating sequence;

E. quantifying at least one of an organic carbon content and a mineral carbon content of the sample as follows:
  i. if the value of the parameter SCmin is less than or equal to a predefined threshold value of the parameter SCmin, the mineral carbon content is zero and the organic carbon content is equal to a sum of the parameters TOC and MinC;
  ii. if the value of the parameter SCmin is greater than the predefined threshold value of the parameter Scmin at least one of:
    the mineral carbon content Cmin is determined according to a formula of the type: Cmin=MinC−k×TOC; and
    the organic carbon content Corg is determined according to a formula of the type: Corg=TOC+k×TOC, where k is a correction factor ranging between 0.04 and 0.12.

According to an implementation of the invention, the predefined threshold value of the parameter SCmin can range between 0.03 and 0.05, and it is preferably equal to 0.04.

According to an implementation of the invention, the correction factor k can preferably be equal to 0.09.

According to an implementation of the invention, the initial temperature (T0) of the first heating sequence can range between 80° C. and 150° C., and it is preferably equal to 150° C.

According to an implementation of the invention, the initial temperature of the second heating sequence can be equal to the initial temperature (T0) of the first heating sequence.

According to an implementation of the invention, the first intermediate temperature of the first heating sequence can be equal to 400° C.

According to an implementation of the invention, the second intermediate temperature of the first heating sequence can be equal to 550° C.

According to an implementation of the invention, the first heating sequence can comprise an additional isothermal stage, at the final temperature (TF) of the first heating sequence.

According to an implementation of the invention, the predetermined duration of the isothermal stage(s) of the first heating sequence can range between 3 and 5 minutes.

According to an implementation of the invention, the thermal gradient of the first heating sequence can range between 1° C. and 50° C. min$^{-1}$, and preferably between 20° C. and 25° C. min$^{-1}$.

According to an implementation of the invention, the thermal gradient of the second heating sequence can range between 20° C. and 40° C. min$^{-1}$, and preferably between 20° C. and 25° C. min$^{-1}$.

BRIEF DESCRIPTION OF THE DRAWINGS

Other features and advantages of the method according to the invention will be clear from reading the description hereafter of embodiments given by way of non-limitative example, with reference to the accompanying figures wherein:

FIGS. 1A and 1B schematically illustrate respectively the heating sequence in an inert atmosphere according to the invention and a heating sequence in an inert atmosphere according to an implementation of the invention;

FIGS. 2A and 2B illustrate thermograms obtained with the heating sequence in an inert atmosphere according to the invention applied to a non-carbonate soil sample;

FIGS. 2C and 2D illustrate thermograms obtained with an implementation of the heating sequence in an inert atmosphere according to the invention applied to a carbonate soil sample;

FIGS. 3A and 3B illustrate thermograms obtained with an implementation of the heating sequence in an oxidizing atmosphere according to the invention, obtained for the non-carbonate soil sample of FIGS. 2A and 2B, and for the carbonate soil sample of FIGS. 2C and 2D respectively; and FIG. 4 illustrates the evolution of a parameter MinC as a function of a parameter TOC determined for samples corresponding to four mineral carbon abundance classes.

DETAILED DESCRIPTION OF THE INVENTION

The invention relates to a method of characterizing and quantifying the carbon (or, in other words, the carbon forms) present in a superficial deposit.

A superficial deposit is understood to be a continental or littoral formation, unconsolidated or with secondary consolidation, resulting from at least one of the mechanical and chemical weathering of pre-existing rocks, and formed at the lithosphere/biosphere/atmosphere interface. A distinction is made between (i) the "allochthonous superficial deposits" (such as colluvium, alluvium, loess, etc.), which have undergone or still undergo close or distant displacements, and no longer rest on their parent material, and (ii) the "autochthonous superficial deposits" (such as grits, alterites, flint clays, etc.), which have evolved locally, from a parent material that still is their substrate.

Soil is understood to be all of the outer layers of superficial deposits, whose properties are directly controlled by the mutual actions of water, air and of living and dead organisms, or even human activities for the most recent periods.

These terms are notably defined in the reference document (Dictionnaire encyclopédique de Science du Sol, Mathieu & Lozet, Lavoisier, 2011).

The method according to the invention requires at least one sample representative of the superficial deposit which may have been taken manually in a trough or by core drilling using an auger bit. Advantageously, the sample as taken is sieved using a sieve with 2 mm diameter orifices, dried at a temperature below 40° C., then crushed until fragments of size less than 200 μm are obtained.

The method according to the invention can advantageously, but without limitation, be implemented using the ROCK-EVAL® device (IFP Energies nouvelles, France) as described in patents FR-2,227,797 (U.S. Pat. No. 3,953,171) and FR-2,472,754 (U.S. Pat. No. 4,352,673). Indeed, the ROCK-EVAL® device comprises at least:

an oven for pyrolysis in a non-oxidizing atmosphere, a device for transferring the pyrolysis residues to an oxidation oven, an oven for oxidation in an oxidizing atmosphere, a device for measuring the quantity of hydrocarbon compounds (HC) released during pyrolysis, and a device for measuring the carbon monoxide (CO) and the carbon dioxide ($CO_2$).

The method can also be implemented using a single pyrolysis oven operating both in a non-oxidizing atmosphere and in an oxidizing atmosphere, cooperating with a device for measuring the quantity of hydrocarbon compounds released during pyrolysis, and a device for measuring the carbon monoxide and the carbon dioxide.

The method according to the invention comprises at least the following steps:

1—Heating sequence in an inert atmosphere (pyrolysis)

2—Heating sequence in an oxidizing atmosphere (oxidation)

3—Characterization and quantification of the carbon present in the sample.

The steps of the method according to the invention are detailed hereafter, without limitation, for a soil sample. Indeed, the steps of the method according to the invention may as well be applied to a sample from another layer of a superficial deposit.

1—Heating Sequence in an Inert Atmosphere (Pyrolysis)

In this step, a soil sample is heated in an inert atmosphere (in a stream of nitrogen, helium, for example) according to a sequence of predefined time-varying temperatures.

According to the invention, the heating sequence in an inert atmosphere comprises at least one isothermal stage of non-zero duration at an initial temperature (denoted by T0 hereafter) ranging between 80° C. and 200° C., followed by a predetermined thermal gradient which raises the temperature up to a final temperature (denoted by TF hereafter) ranging between 600° C. and 650° C. For this embodiment, the heating sequence can preferably comprise only one isothermal stage and thermal gradient. FIG. 1A schematically illustrates the evolution of temperature T as a function of time t of such a sequence of temperatures, with an isothermal stage at temperature T0, followed by a thermal gradient up to temperature TF.

Preferably, the heating sequence in an inert atmosphere further comprises a second isothermal stage, at final temperature TF. In other words, a second isothermal stage at final temperature TF follows the phase of the heating sequence in form of a thermal gradient. This allows, if need be, to continue cracking of the compounds having a cracking temperature close to final temperature TF of the heating sequence in an inert atmosphere according to the invention. FIG. 1B schematically illustrates the evolution of temperature T as a function of time t of such a sequence of temperatures, with two isothermal stages, at temperatures T0 and TF as defined above. For this embodiment, the heating sequence can preferably comprise only two isothermal stages and one thermal gradient.

According to an implementation of the invention, the first isothermal stage can preferably be at a temperature ranging between 80° C. and 150° C., so as to enable recovery of the contributions of the most labile organic compounds present in a soil sample. Preferably, the first isothermal stage is at a value of 150° C., which is a sufficient temperature for recovery of the contributions of the most labile organic compounds present in most soil samples.

According to an implementation of the invention, final temperature TF is preferably equal to 600° C. Such a temperature makes it possible to avoid CO and $CO_2$ curves with incomplete peaks at the end of pyrolysis, notably when the maximum temperature reaches 650° C., in particular with plant samples (litters, peats, composts).

According to the invention, the predetermined duration of an isothermal stage is non-zero (greater than half a minute for example), and it can preferably range between 3 and 5 minutes. Such durations allow consideration of cracking of the compounds having a cracking temperature close to the temperature of the isothermal stage is completed. According to the implementation of the invention wherein the heating sequence in an inert atmosphere according to the invention comprises several isothermal stages and, in particular, two isothermal stages at temperatures T0 and TF, the duration of an isothermal stage can be different from the duration of the other isothermal stage(s).

According to an implementation of the invention, the thermal gradient can range between 1° C. and 50° C.min-$^1$, preferably between 20° C. and 25° C.min$^1$. Such values are compromises allowing thermal cracking of the compounds while limiting the duration of implementation of the method.

According to the invention, a quantity of hydrocarbon compounds released during heating in an inert atmosphere, and the quantity of $CO_2$ and CO contained in the effluent resulting from the heating are also continuously measured. In other words, during this sequence, the quantity of HC, CO and $CO_2$ released by the sample by thermal cracking of the organic matter and by the thermal decomposition of the carbonate minerals is continuously measured. Thus, a first curve representative of the quantity of hydrocarbon compounds released over time during the pyrolysis phase, and two other curves representative of the quantity of CO and $CO_2$ released over time during the pyrolysis phase, are obtained at the end of this step applied to a given sample. Measuring the quantity of hydrocarbon compounds can be done using a flame ionization type detector (FID). Measuring the quantity of CO and $CO_2$ released can be done using an infrared (IR) type detector. It should be noted that such detectors measure a stream of HC, CO and/or $CO_2$, and that they give values measured in millivolt (mV). Conventionally, a quantity of at least one of HC, CO and $CO_2$ can be determined by determining an area under the curve measured (possibly between predefined temperatures) by these detectors, and by dividing this area by the mass in mg of the sample. As a variant, other devices for measuring the quantity of at least one of HC, CO and $CO_2$ can be used.

In general, this particular heating sequence in an inert atmosphere is sufficient to enable thermal cracking of the compound classes comprising mineral carbon and organic carbon, notably:

the thermally very labile compounds, which are particularly abundant in fresh biological tissues, and generally released at temperatures ranging between about 80° C. and 360° C.;

the thermally labile compounds, which predominate in organic samples such as litters or peats, and are generally released at temperatures ranging between about 360° C. and 420° C.;

the thermally resistant compounds, predominant in organo-mineral (soils) or mineral (alluvium, colluvium) samples, which are generally released at temperatures ranging between about 420° C. and 470° C.;

the thermally refractory compounds, generally released at temperatures ranging between about 470° C. and 520° C.; and the thermally very refractory compounds, which are present in larger proportions in decomposition residues or in exogenous fractions, such as pyrogenic or petrogenic organic matter, and which are generally released at temperatures ranging between about 520° C. and 650°.

According to an implementation of the invention, the heating sequence in an inert atmosphere according to the invention can be preceded by a pyrolysis oven temperature rise phase, which can be a thermal gradient ranging, for example, between 1° C. and 50° C.min$^{-1}$, preferably between 20° C. and 25° C.min$^{-1}$, or of any other form of temperature rise curve of the pyrolysis oven. This preliminary phase of pyrolysis oven temperature rise allows the pyrolysis oven to be brought to the temperature of the first isothermal stage of the heating sequence in an inert atmosphere according to the invention. This preliminary phase can contribute to starting thermal cracking of the compounds whose cracking temperature is less than the temperature of the first isothermal stage, notably in the case of fresh biological tissues.

According to an implementation of the invention, the heating sequence in an inert atmosphere according to the invention can be followed by a phase of lowering the pyrolysis oven temperature, which can be in form of a thermal gradient ranging for example between −1° C. and −50° C.min$^{-1}$, preferably between −20° C. and −25° C. min$^{-1}$, or of any other form of temperature decrease curve of the pyrolysis oven. This end phase of lowering the pyrolysis oven temperature enables, if need be, to complete thermal cracking of the compounds associated with the last isothermal stage of the heating sequence in an inert atmosphere according to the invention.

According to the invention, two intermediate temperatures (denoted by TIP1 and TIP2 hereafter) ranging between initial temperature T0 and final temperature TF of the heating sequence in an inert atmosphere are defined. More precisely, the first intermediate temperature of the heating sequence in an inert atmosphere ranges between 370° C. and 430° C., and it is preferably 400° C. The second intermediate temperature of the heating sequence in an inert atmosphere ranges between 520° C. and 580° C., and it is preferably 550° C. These temperatures are conventionally used in the prior art to define respective $CO_2$ and CO quantities involved in the determination of standard parameters TOC and MinC.

FIGS. 2A and 2B (respectively 2C and 2D) illustrate thermograms obtained by carrying out the heating sequence in an inert atmosphere according to the invention applied to a non-carbonate soil sample (respectively a carbonate soil sample). More precisely, in these figures, curve T represents the evolution as a function of time t of the pyrolysis oven temperature during this step or, in other words, curve T represents the heating sequence in an inert atmosphere to which the samples are subjected. It can be noted in these figures that the heating sequence in an inert atmosphere carried out for these samples starts with a first stage at 200° C., followed by a thermal gradient allowing the temperature to be raised up to a final temperature of 650° C. This heating sequence in an inert atmosphere comprises an end phase of lowering the pyrolysis oven temperature. Besides, in these figures, curve HC (FIGS. 2A and 2C) represents the evolution of the intensity QHC (in mV) of the signal of a detector FID measuring the quantity of hydrocarbon compounds released during the heating sequence in an inert atmosphere, curve CO (FIGS. 2B and 2D) represents the evolution of intensity QCO (in mV) of the signal of an IR detector measuring the quantity of CO released during the heating sequence in an inert atmosphere, and curve $CO_2$ (FIGS. 2B and 2D) represents the evolution of intensity QCO2 (in mV) of the signal of an IR detector measuring the quantity of $CO_2$ released during the heating sequence in an inert atmosphere. It can be noted that curve HC of FIG. 2A has a main peak around 800 s and a shoulder around 480 s, whereas curve HC of FIG. 2C has a wide peak around 780 s, which is explained by the relative contributions of the constituent classes cracking around the corresponding temperatures, the thermally stable constituents (cracking around 800 s) being relatively more abundant in the first case than in the second. Conventionally, two portions are seen in the curve relative to the $CO_2$ released during the heating sequence in an inert atmosphere of FIGS. 2B and 2D: a first portion to the left of first intermediate temperature TIP1, equal to 400° C. here, denoted by S3, which is conventionally (but wrongly in the case of superficial deposits) considered to correspond to the $CO_2$ generated by cracking of the organic matter of the sample during heating in an inert atmosphere, and a second portion to the right of first intermediate temperature TIP1, denoted by S3', which is conventionally (but wrongly in the case of superficial deposits) considered to correspond to the $CO_2$ generated by cracking of the mineral matrix during heating in an inert atmosphere. Two portions can also be distinguished in the curve relative to the CO released during the heating sequence in an inert atmosphere of FIGS. 2B and 2D: a first portion to the left of second intermediate temperature TIP2, substantially equal to 550° C. here, denoted by S3CO, which is conventionally (but wrongly in the case of superficial deposits) considered to correspond to the CO generated by cracking of the organic matter of the sample during heating in an inert atmosphere, and a second portion to the right of this second intermediate temperature TIP2, denoted by S3' CO, which is conventionally considered to correspond to a mixture of CO generated by cracking of the organic matter and by the thermal decomposition of the mineral matrix during heating in an inert atmosphere. It can be noted that curves $CO_2$ and CO of FIG. 2B have a peak around 1260 s, poorly marked in relation to those observed in curves $CO_2$ and CO of FIG. 2D, which is explained by the $CO_2$ and CO contribution related to the decomposition of the carbonates in the carbonate soil sample.

2—Heating Sequence in an Oxidizing Atmosphere (Oxidation)

In this second step, the solid sample residue obtained at the end of the heating sequence in an inert atmosphere as described in step 1 above is subjected to oxidation according to a predefined time-varying temperature program.

The temperature program of the heating sequence in an oxidizing atmosphere according to the invention is as follows: from a temperature (denoted by T'min hereafter) ranging between 150° C. and 300° C., preferably ranging between 150° C. and 250° C., and preferably equal to 150° C. or more preferably equal to the temperature of the first isothermal stage of the heating sequence in an inert atmosphere so as to be able to make comparisons, the temperature of the sample residue from step 1 is increased according to a temperature gradient preferably ranging between 20° C. and 40° C.min$^{-1}$, more preferably between 20° C. and 25° C.min$^{-1}$, up to an oxidation end temperature (denoted by T'max hereafter) ranging between 850° C. and 1200° C., preferably equal to 900° C., so as to deplete the mineral carbon stock.

According to the invention, representative quantities of CO and $CO_2$ released during this second heating sequence are continuously measured. According to an implementation of the invention, this measurement can be performed using an infrared (IR) type detector. It should be noted that such a detector measures a stream of CO and/or $CO_2$, and it provides values measured in millivolt (mV). Conventionally, a quantity of CO and/or $CO_2$ is determined by determining an area under the curve (possibly between predefined temperatures) measured by this detector, and this area is divided by the mass in mg of the sample. As a variant, other devices for measuring the quantity of at least one of CO and $CO_2$ can be used.

In general, the preferred temperature range for the initial temperature T'min of the heating sequence in an oxidizing atmosphere, lower than the initial temperatures known from the prior art (generally 300° C.), makes it possible to avoid episodes of instantaneous combustion of the sample residue at the beginning of the oxidation cycle.

According to the invention, an intermediate temperature (denoted by TLO hereafter) ranging between initial temperature T'min and final temperature T'max of the heating sequence in an oxidizing atmosphere, more precisely ranging between 620° C. and 680° C., and preferably equal to 650° C., is defined. It is a temperature that is conventionally used in the prior art to define quantities involved in the determination of standard parameters TOC and MinC.

FIGS. 3A and 3B illustrate thermograms obtained by the heating sequence in an oxidizing atmosphere according to the invention, respectively for the non-carbonate soil sample of FIGS. 2A and 2B, and for the carbonate soil sample of FIGS. 2C and 2D. More precisely, in these figures, curve T' represents the evolution over time t of the oxidation oven temperature during this step or, in other words, curve T' represents the heating sequence in an oxidizing atmosphere to which the sample residues are subjected. Besides, curve $CO_2$ (respectively curve CO) represents the evolution of intensity QCO$_2$ in mV (respectively QCO) of the signal of an IR detector measuring the quantity of $CO_2$ (respectively CO) released over time by the residue from step 1 and subjected to the heating sequence in an oxidizing atmosphere T'. Conventionally, the portion of curve $CO_2$ (respectively curve CO) to the left of intermediate oxidation temperature TLO, substantially equal to 650° C. here, which is conventionally considered to correspond to the $CO_2$ (respectively the CO) generated by cracking of the organic matter of the sample residue during heating in an oxidizing atmosphere, is denoted by S4CO$_2$ (respectively S4CO). Conventionally, the portion of curve $CO_2$ to the right of intermediate oxidation temperature TLO, which is conventionally considered to correspond to the $CO_2$ generated by the decomposition of the carbonate minerals of the sample residue during heating in an oxidizing atmosphere, is denoted by S5. $CO_2$ streams above a temperature of about 650° C., which are specific to carbonate soils and testify to the presence of mineral carbon forms, can be observed in these FIGS. 3A and 3B. It can also be noted that curve CO ends in both cases around intermediate temperature TLO.

3—Characterization and Quantification of the Carbon Present in the Sample

This step characterizes and in quantifies the carbon present in the soil sample, and notably in determining at least one of an organic carbon content and a mineral carbon content. This step comprises at least the two substeps detailed hereafter.

3.1 Determination of a Parameter Characterizing the Mineral Carbon Proportion in the Sample According to the invention, this first substep determines a parameter characterizing the proportion of mineral carbon in relation to the total carbon present in the sample considered, from the quantity of $CO_2$ measured in step 2 described above.

More precisely, according to the invention, a parameter SCmin representative of a proportion of mineral carbon in relation to the total carbon in the sample is determined from a ratio between the quantity of $CO_2$ released by the sample residue above intermediate temperature TLO of the heating sequence in an oxidizing atmosphere described above, and the total quantity of $CO_2$ released by this residue during the heating sequence in an oxidizing atmosphere. Thus, parameter SCmin is defined by the proportion of $CO_2$ released by thermal decomposition of the mineral carbon contained in the sample during the heating sequence in an oxidizing atmosphere in relation to the total quantity of $CO_2$ released during this heating sequence in an oxidizing atmosphere.

According to an implementation of the invention, parameter SCmin can be determined according to a formula of the type:

$$SC\min = \frac{S5}{S4CO2 + S5}$$

where S5 and $S4CO_2$ are defined in the previous step. In general, term S5 very predominantly corresponds to the $CO_2$ released by decomposition of the carbonate mineral species, and term $S4CO_2$ corresponds to the quantity of $CO_2$ released by combustion of the residual organic carbon from the pyrolysis during the oxidation phase.

According to the invention, a threshold value is defined for parameter SCmin, below which it may be considered that the soil sample is devoid of mineral carbon form (i.e. it is a non-carbonate sample) or, in other words, below which it may be considered that any carbon form contained in this sample is of organic nature.

According to an implementation of the invention, the threshold value of parameter SCmin, denoted by SCmin_seuil, according to which the soil sample considered is devoid of mineral form, can range between 0.03 and 0.05, and it is preferably equal to 0.04. These values correspond to errors related to the implementation of the method of the invention, due to the measuring device itself and to the determination of quantities of $CO_2$ released below and above intermediate temperature TLO defined in the previous step.

According to an implementation of the invention, the carbon of a sample can further be characterized by defining four abundance classes for the mineral forms of carbon of a sample, and the abundance classes can be defined according to the value of parameter SCmin of the invention as follows:

if SCmin<0.04: the sample comprises no mineral form of carbon, this class is denoted by SCmin1 hereafter;
if 0.04<SCmin<0.2: the sample comprises mineral forms of carbon as traces, this class is denoted by SCmin2 hereafter;
if 0.2<SCmin<0.6: the sample comprises mineral forms of carbon, this class is denoted by SCmin3 hereafter; and
if SCmin>0.6: the sample comprises mineral forms of carbon in abundance, this class is denoted by SCmin4 hereafter.

3.2 Determination of at Least One of an Organic Carbon Content and of a Mineral Carbon Content This step determines at least one of an organic carbon content and/or a mineral carbon content from the quantities of HC, CO and $CO_2$ measured in steps 1 and 2 as described above, and according to the value of parameter SCmin described in substep 3.1 above.

According to the invention, the conventional parameters TOC and MinC defined in the prior art are first determined, then at least one of the organic carbon and mineral carbon content is determined from corrections applied to these conventional parameters, because they are not suited to superficial deposit samples. Moreover, according to the invention, the corrections to be brought to the standard parameters depend on the value of parameter SCmin in relation to threshold value SCmin_seuil defined in the previous substep.

According to the invention, parameter TOC and parameter MinC as known in the prior art, and notably from document (Behar et al., 2001), are determined with formulas of the type:

$$TOC = [S2*0.083] + \left[S3*\frac{12}{440}\right] + \left[\left(S3CO + \frac{S3'CO}{2}\right)*\frac{12}{180}\right] + \left[S4CO_2*\frac{12}{440}\right] + \left[S4CO*\frac{12}{280}\right]$$

$$\mathrm{Min}\,C = \left[S3'*\frac{12}{440}\right] + \left[\frac{S3'CO}{2}*\frac{12}{280}\right] + \left[S5*\frac{12}{440}\right]$$

According to the invention, two possible cases are defined depending on the value of parameter SCmin:

a) First Case: SCmin≤SCmin_Seuil

According to the invention, if the value of parameter SCmin is less than or equal to threshold value SCmin_seuil defined in the previous substep (i.e. if the sample considered is a non-carbonate sample), then the definitions are:

a mineral carbon content according to the formula: Cmin=0; and
an organic carbon content according to the formula: Corg=TOC+MinC.

Thus, contrary to what is taught by the prior art, which calculated a non-zero parameter MinC even in the absence of mineral carbon in the sample, the present invention allows to determine a mineral carbon content representative of the real mineral carbon content of a sample of a superficial deposit without mineral form of carbon. In addition, the organic carbon content according to the invention is determined by accounting for, unlike the prior art, the total quantities of CO and $CO_2$ released during the heating sequences in an inert atmosphere and in an oxidizing atmosphere. Indeed, determination of the organic carbon content according to the prior art only considered the quantities of CO and $CO_2$ released below intermediate temperatures TTIP1 and TIP2 of the heating sequence in an inert atmosphere defined in step 1, half of the quantity of CO released above intermediate temperature TIP2, and the quantities of CO and $CO_2$ released below intermediate temperature TLO of the heating sequence in an oxidizing atmosphere defined in step 2.

b) Second Case: SCmin>SCmin_Seuil

According to the invention, if the value of parameter SCmin is greater than threshold value SCmin_seuil defined in the previous substep (i.e. if the sample considered is a carbonate sample), then it is defined as:

a mineral carbon content according to the formula:
Cmin=MinC–k×TOC;

an organic carbon content according to the formula:
Corg=TOC+k×TOC, where k is a correction factor ranging between 0.04 and 0.12, and preferably equal to 0.09.

In other words, the organic carbon content is equal to the sum of the TOC and of the thermally stable organic fraction whose value is estimated between 4% and 12% of the TOC, preferably 9%, and the organic carbon content is equal to MinC minus this thermally stable fraction of organic nature.

These corrections have been established from samples (approximately 50) from superficial deposits with very varied organic and mineral carbon proportions, more precisely for values of parameter SCmin varying in the 4 abundance classes SCmin1 to SCmin4 described above. For each of these samples, the conventional parameters TOC and MinC according to the prior art, defined above, have been determined. FIG. 4 shows the evolution of parameter MinC as a function of parameter TOC determined according to the prior art for the plurality of samples. A very strong linear correlation (line REG) can be observed in this figure between parameters TOC and MinC for the samples of classes SCmin1 and SCmin2. On the other hand, the dispersion is much larger for samples wherein mineral carbon forms are present or abundant (class SCmin3), until the relation is no longer significant for the samples of class SCmin4. A linear regression applied for each class SCmin1 to SCmin4 leads to the following relations between parameters TOC and MinC:

$$MinC=0.09×TOC, \text{ with } R^2=0.96 \text{ and } p<4.10^{-11} \qquad SCmin1$$

$$MinC=0.15×TOC \text{ with } R^2=0.93 \text{ and } p<1.10^{-9} \qquad Scmin2$$

$$MinC=0.42×TOC \text{ with } R^2=0.77 \text{ and } p<0.002 \qquad SCmin3$$

$$MinC=3.03×TOC, \text{ with } R^2=0.35 \text{ and } p>0.05, \qquad SCmin4$$

where $R^2$ corresponds to the coefficient of determination of the linear regression, and p corresponds to a probability of obtaining the same value or an even a more extreme value than the one observed.

The relation established for category SCmin1 reflects the fact that, in these samples without mineral carbon form, all of the carbon counted in MinC is a thermally stable fraction of the organic carbon. Besides, although the panel of samples covers highly varied situations, the dispersion around the regression line is very low ($R2=0.96$ and $p<4.10-11$), which indicates that the thermally stable organic fraction is identical in all soils (about 9% of the TOC). It may therefore be considered as a general property, independent of pedogenetic contexts. For the other mineral carbon abundance classes SCmin2, SCmin3, SCmin4, it is reasonable to consider that this property is verified, but that it is increasingly hidden by the growing proportion of the mineral forms of carbon, as evidenced by the concomitant increase of the slope coefficient of the regression line and of the point cloud dispersion. It is therefore legitimate to generalize in first approximation the relation established for class SCmin1 to all the mineral carbon abundance classes of the superficial deposits.

Thus, the definitions of the mineral carbon and organic carbon contents according to the invention account for the carbon forms present as follows: (i) all the carbon forms are organic in the samples such that SCmin≤SCmin_seuil, and (ii) the other mineral carbon abundance classes comprise a thermally stable organic carbon part, plus a mineral carbon part.

Thus, after these two substeps, a reliable characterization and quantification of the carbon present in a superficial deposit sample is obtained via the determination of a parameter SCmin representing a proportion of mineral carbon in the sample, and the determination of at least one of the organic carbon and mineral carbon content of the sample from corrections brought to parameters TOC and MinC determined according to the prior art.

3.3 Determination of the Thermal Status of Organic Carbon Forms

This substep, which is optional, is determining the thermal status of the organic carbon forms in the sample. The thermal status of the organic carbon forms present in the sample is understood to be an indicator of the distribution of the various compound classes present in the sample, with each defined by the cracking temperature thereof.

The organic matter of a soil is a complex heterogeneous mixture comprising constituents of various natures and origins which are residues from the gradual decomposition of the most labile biogenic constituents, free particles and constituents involved in organo-mineral complexes, pyrogenic or petrogenic constituents. The thermal fractionation method according to the invention does not allow these specific constituents to be separated. On the other hand, it makes possible measurement of the contributions of compound classes defined each by their cracking temperature. Thermal stability being considered as a variable related to biogeochemical stability (that is the resistance to decomposition by micro-organisms), the contributions of the defined compound classes can be used to describe the heterogeneity of the organic matter of soils.

We introduce hereafter the notations defined in Tables 1 and 2 below:

Subsequently, the parameters defined in Table 1 below can be used. More precisely, parameters $S2_i$ ($S3CO2_i$ and $S3CO_i$ respectively), with i ranging from 0 to 6, correspond to the quantities of HC (respectively $CO_2$ and CO) released in the temperature ranges $DT_i$ defined as follows: $DT_0=T0-$; $T0<DT_1\leq T1$; $T1<DT_2\leq T2$; $T2<DT_3\leq T3$; $T3<DT_4\leq T4$; $T4<DT_5\leq T5$; $DT_6=TF+$; and where $T0-$ corresponds to the first isothermal stage at temperature T0 of the heating sequence in an inert atmosphere, possibly preceded by a preliminary phase of temperature rise of the pyrolysis oven; and where TF+ corresponds to the final temperature TF of the heating sequence in an inert atmosphere, possibly followed by an isothermal stage end phase at temperature TF, or by a phase of lowering the pyrolysis oven temperature; and where T1 is an intermediate temperature ranging between 320° C. and 360° C., T2 is an intermediate temperature ranging between 400° C. and 440° C. (alternatively ranging between 380° C. and 420° C.), T3 is an intermediate temperature ranging between 380° C. and 420° C. (alternatively ranging between 440° C. and 480° C.), T4 is an intermediate temperature ranging between 440° C. and 480° C. (alternatively ranging between 500° C. and 540° C.), and T5 is an intermediate temperature ranging between 500° C. and 540° C. (alternatively ranging between 600° C. and 650° C.). These intermediate temperatures correspond to relative minima observed on HC, CO and $CO_2$ curves measured for a plurality of samples of superficial deposits, notably of soils of various natures and origins.

TABLE 1

| Temperature | HC measurement | $CO_2$ measurement | CO measurement |
|---|---|---|---|
| $DT_0 = T0-$ | $S2_0$ | $S3CO2_0$ | $S3CO_0$ |
| $T0 < DT_1 \leq T1$ | $S2_1$ | $S3CO2_1$ | $S3CO_1$ |
| $T1 < DT_2 \leq T2$ | $S2_2$ | $S3CO2_2$ | $S3CO_2$ |
| $T2 < DT_3 \leq T3$ | $S2_3$ | $S3CO2_3$ | $S3CO_3$ |
| $T3 < DT_4 \leq T4$ | $S2_4$ | $S3CO2_4$ | $S3CO_4$ |
| $T4 < DT_5 \leq T5$ | $S2_5$ | $S3CO2_5$ | $S3CO_5$ |
| $DT_6 = T5+$ | $S2_6$ | $S3CO2_6$ | $S3CO_6$ |

Subsequently, the parameters defined in Table 2 below can further be used. More precisely, parameters $S4CO2_i$ and $S4CO_i$, with i ranging from 0 to 4, correspond to the quantities of $CO_2$ and CO released in the temperature ranges DT'i defined as follows: DT'0≤T'min; T'min<DT'1≤T'int1; T'int1<DT'2≤T'int2; T'int2<DT'3≤T'int3 and T'int3<DT'4≤T'max, where T'int1, T'int2 and T'int3 are intermediate temperatures ranging between T'min and T'max, such that T'int1 ranges between 420° C. and 480° C. and is preferably equal to 460° C., T'int2 ranges between 520° C. and 580° C. and is preferably equal to 550° C., and T'int3 ranges between 630° C. and 670° C. and is preferably equal to 650° C. These intermediate temperatures correspond to relative minima observed by the applicant on CO and $CO_2$ curves measured for samples from superficial deposits, notably soils of various nature and origins. Considering that, according to the literature, the combustion temperature is an approximation of thermal stability, the CO and $CO_2$ streams measured in temperature ranges DT' 1, DT'2 and DT'3 can be related to organic constituent classes of increasing stability. Considering that the thermal stability limit of calcite is close to T'int3, the $CO_2$ streams measured in temperature range DT'4 can be related to mineral carbon forms.

TABLE 2

| $DT'_0 \leq T'min$ | $S4CO2_0$ | $S4CO_0$ |
|---|---|---|
| $T'min < DT'_1 \leq T'int1$ | $S4CO2_0$ | $S4CO_1$ |
| $T'int1 < DT'_2 \leq T'int2$ | $S4CO2_2$ | $S4CO_2$ |
| $T'int2 < DT'_3 \leq T'int3$ | $S4CO2_3$ | $S4CO_3$ |
| $T'int3 < DT'_4 \leq T'max$ | $S4CO2_4$ | $S4CO_4$ |

According to a first embodiment of this variant of the invention comprising a substep of determining the thermal status of the carbon forms of the sample, a decomposition index ID and a stability index IS can be defined from the contributions of the compound classes defined above, with formulas of the type:

decomposition index $ID = \log[S2_1 + S2_2]/S2_3$ stability index $IS = [S2_3 + S2_4 + S2_5 + S2_6]/100.$ Thus, these two indices are directly related to the most reactive fraction of the organic carbon (that is the pyrolyzed carbon part in form of hydrocarbon compounds).

Stability index IS measures the relative contributions of the thermally stable compound classes ($S2_3$, $S2_4$, $S2_5$ and $S2_6$) that are particularly abundant in superficial deposits and in the deep layers of soils, in contrast to the more labile compound classes ($S2_1$ and $S2_2$) that are more abundant in poorly decomposed plant tissues present in the organic layers and the superficial layers of soils.

Decomposition index ID measures the ratio between these most labile compound classes ($S2_1$ and $S2_2$) and the intermediate compound class ($S2_3$), which is particularly abundant in the organic and organo-mineral layers of soils. In general, decomposition index ID measures the degree of transformation of the organic matter as the compounds of the most labile compound classes are decomposed and the compounds of the most stable compound classes accumulate.

According to a second embodiment of this variant of the invention comprising a substep of determining the thermal status of the carbon forms of the sample, the thermal status of the carbon forms of a sample is determined from the relative contributions of the various compound classes of a sample to calculate a thermally labile (i.e. resulting from thermal cracking and combustion below T3) organic carbon content Corg and a thermally stable (i.e. resulting from thermal cracking and combustion below T3) organic carbon content Corg.

According to an implementation of the invention, at least one of the following parameters characterizing the thermal status of the sample can be determined:
a thermally labile pyrolyzed organic carbon content, denoted by COPL, defined according to a formula of the type:

$$COPL\ (\%\ C) =$$
$$(S2_L \times 0.083) + \left([KCOPL * S3CO2_L] \times \frac{12}{440}\right) + \left(S3CO_L \times \frac{12}{280}\right)$$

with KCOPL ranging between 1 and 2, preferably equal to 1.3359
a thermally stable pyrolyzed organic carbon content, denoted by COPS, defined according to a formula of the type:

$$COPS\ (\%C) =$$
$$(S2_S x\ 0.083) + \left([KCOPS(S3CO2_L]x\frac{12}{440}\right) + \left([1/2\ S3CO_S]x\frac{12}{280}\right)$$

with KCOPS ranging between 0.1 and 1, preferably equal to 0.6274
a thermally labile residual organic carbon content, denoted by CORL, defined according to a formula of the type:

$$CORL\ (\%\ C) = \left(S4CO2_L \times \frac{12}{440}\right) + \left(S4CO_L \times \frac{12}{280}\right)$$

a thermally stable residual organic carbon content, denoted by CORS, defined according to a formula of the type:

$$CORS\ (\%\ C) = \left(S4CO2_S \times \frac{12}{440}\right)$$

where $S2_L = \sum_{i=0}^{i=3} S2_i$;

$S2_S = \sum_{i=4}^{i=6} S2_i$ $S3CO2_L = \sum_{i=0}^{i=3} S3CO2_i$;

$S3CO2_S = \sum_{i=4}^{i=6} S3CO2_i$;

-continued $$S3CO_L = \sum_{i=0}^{i=4} S3CO_i;$$

$$S3CO_S = \sum_{i=5}^{i=6} S3CO_i;$$

$$S4CO2_L = \sum_{i=0}^{i=1} S4CO2_i;$$

$$S4CO2_S = \sum_{i=2}^{i=3} S4CO2_i;$$

$$S4CO_L = \sum_{i=0}^{i=1} S4CO_i;$$

$$S4CO_S = \sum_{i=2}^{i=3} S4CO_i.$$

These partial contents are particularly useful to understand the dynamics of organic matter in soils, because they allow to compare the total organic carbon stocks with the contributions of the various carbon forms, and to monitor the evolution of these stocks over time. They notably allow exploration of the relations between the thermally labile organic carbon and the thermally stable organic carbon stocks that are directly correlated in soils, which indicates that transfer from one stock to the other actually takes place in the soils.

Thus, the present invention allows simple, fast and reliable characterization and quantification of the carbon forms present in a sample of a superficial deposit, whether the superficial deposit is a carbonate deposit or not. In particular, the present invention defines at least one of organic carbon and mineral carbon contents taking into account an estimated quantity of $CO_2$ released by thermal cracking of the organic matter of the sample during the heating sequence in an inert atmosphere above a temperature considered to be an intermediate temperature in the prior art.

The invention claimed is:

1. A method of characterizing and quantifying carbon present in a superficial deposit, from a sample representative of the superficial deposit, comprising:

A. heating the sample according to a first heating sequence in an inert atmosphere, and continuously measuring a quantity of hydrocarbon compounds, a quantity of CO and a quantity of $CO_2$ released during the first heating sequence, the first heating sequence in an inert atmosphere comprising at least one isothermal stage of predetermined duration at an initial temperature followed by a thermal gradient in order to reach a final temperature, the initial pyrolysis temperature temperature ranging between 80° C. and 200° C., the final pyrolysis temperature ranging between 600° C. and 650° C.;

B. heating a residue of the sample from the first heating sequence according to a second heating sequence in an oxidizing atmosphere, and measuring a quantity of CO and a quantity of $CO_2$ released during the second heating sequence, the second heating sequence in an oxidizing atmosphere starting at an initial temperature ranging between 150° C. and 300° C., and ending at a final temperature ranging between 850° C. and 1200° C., following a thermal gradient;

C. determining a value of a parameter SCmin representative of a mineral carbon proportion in relation to total carbon of the sample, from a ratio between a quantity of $CO_2$ released by the residue of the sample above an intermediate temperature of the second heating sequence ranging between 620° C. and 680° C., and the quantity of $CO_2$ released by the residue during the second heating sequence;

D. from the measurements of the quantities of HC, CO and $CO_2$ released during the first and second heating sequences, determining parameters defined with formulas of a type:

$$TOC = [S2 * 0.083] + \left[S3 * \frac{12}{440}\right] + \left[\left(S3CO + \frac{S3'CO}{2}\right) * \frac{12}{180}\right] + \left[S4CO_2 * \frac{12}{440}\right] + \left[S4CO * \frac{12}{280}\right]$$

$$Min\, C = \left[S3' * \frac{12}{440}\right] + \left[\frac{S3'CO}{2} * \frac{12}{280}\right] + \left[S5 * \frac{12}{440}\right]$$

where S2 represents the quantity of HC released during the first heating sequence, S3 and S3' represent the quantities of $CO_2$ released during the first heating sequence respectively up to and above a first intermediate temperature of the first heating sequence ranging between 370° C. and 430° C., S3CO and S3'CO represent the quantities of CO released during the first heating sequence respectively up to and above a second intermediate temperature of the first heating sequence ranging between 520° C. and 580° C., S4CO2 and S4CO represent the quantities respectively of $CO_2$ and CO released during the second heating sequence up to the intermediate temperature of the second heating sequence, and S5 represents the quantity of $CO_2$ released during the second heating sequence above the intermediate temperature of the second heating sequence;

E. quantifying at least one of an organic carbon content and a mineral carbon content of the sample by a determination:

i. if the value of the parameter SCmin is less than or equal to a predefined threshold value of the parameter SCmin, the mineral carbon content is zero and the organic carbon content is equal to a sum of the parameters TOC and MinC;

ii. if the value of the parameter SCmin is greater than the predefined threshold value of the parameter SCmin:

the mineral carbon content Cmin is determined according to a formula: Cmin=MinC−kxTOC; and the organic carbon content Corg is determined according to a formula: Corg=TOC+kxTOC, where k is a correction factor ranging between 0.04 and 0.12.

2. A method as claimed in claim 1, wherein the predefined threshold value of the parameter Scmin ranges between 0.03 and 0.05.

3. A method as claimed in claim 2, the threshold value is equal to 0.04.

4. A method as claimed in claim 1, wherein correction factor k is equal to 0.09.

5. A method as claimed in claim 2, wherein correction factor k is equal to 0.09.

6. A method as claimed in claim 2, wherein correction factor k is equal to 0.09.

7. A method as claimed in claim 3, wherein correction factor k is equal to 0.09.

8. A method as claimed in claim 1, wherein the initial temperature (T0) is 150° C.

9. A method as claimed in claim 8, wherein the initial temperature of the first heating sequence is 80° C.

10. A method as claimed in claim 1, wherein the initial temperature of the second heating sequence is equal to the initial temperature of the first heating sequence.

11. A method as claimed in claim 1, wherein the first intermediate temperature of the first heating sequence is equal to 400° C.

12. A method as claimed in claim 1, wherein the second intermediate temperature of the first heating sequence is equal to 550° C.

13. A method as claimed in claim 1, wherein the first heating sequence comprises an additional isothermal stage at a final temperature of the first heating sequence.

14. A method as claimed in claim 1, wherein the predetermined duration of each isothermal stage of the first heating sequence ranges between 3 and 5 minutes.

15. A method as claimed in claim 1, wherein the thermal gradient of the first heating sequence ranges between 1° C. and 50° C. $\text{min}^{-1}$.

16. A method in accordance with claim 15, wherein the first heating sequence ranges between 20° C. and 25° C. $\text{min}^{-1}$.

17. A method in accordance with claim 1, wherein the thermal gradient of the second heating sequence ranges between 20° C. and 40° C. $\text{min}^{-1}$.

18. A method in accordance with claim 15, wherein the second heating sequence ranges between 20° C. and 25° C. $\text{min}^{-1}$.

* * * * *